United States Patent [19]
Buchanan et al.

[11] Patent Number: 5,283,270
[45] Date of Patent: Feb. 1, 1994

[54] GLYCIDYL DIAMINES CONTAINING AROMATIC TRIFLUOROMETHYL GROUP AND EPOXY RESINS PREPARED THEREFROM

[75] Inventors: Robert A. Buchanan, Grand Island; Robert L. Ostrozynski, E. Amherst, both of N.Y.

[73] Assignee: Occidental Chemical Corporation, Niagara Falls, N.Y.

[21] Appl. No.: 13,863

[22] Filed: Feb. 5, 1993

[51] Int. Cl.⁵ .................. C08G 59/28; C08G 59/30; C08G 59/32
[52] U.S. Cl. ........................ 523/466; 528/99; 528/220; 528/229; 528/373; 528/391; 528/402; 549/552
[58] Field of Search .............. 549/552; 523/466; 528/99, 220, 229, 391, 402, 373

[56] References Cited
U.S. PATENT DOCUMENTS

| | | | |
|---|---|---|---|
| 2,884,406 | 4/1959 | Wegler et al. | 528/418 |
| 2,951,822 | 9/1960 | Reinking | 549/552 |
| 4,451,645 | 5/1984 | Johncock | 549/552 |
| 4,996,278 | 2/1991 | Lee | 528/26 |

FOREIGN PATENT DOCUMENTS
0076584  4/1983  European Pat. Off.

OTHER PUBLICATIONS
British Polymer Journal, vol. 15, pp. 14–18 (Mar. 1983), "Epoxy Systems with Improved Water Resistance and the Non-Fickian Behavior of Epoxy Systems During Water Ageing", P. Johncock et al.

*Primary Examiner*—Frederick Krass
*Attorney, Agent, or Firm*—Wayne A. Jones; Richard D. Fuerle

[57] ABSTRACT

Disclosed are glycidyl diamines having the formulas

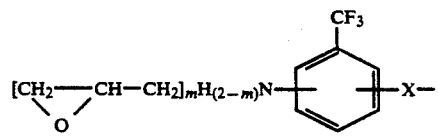

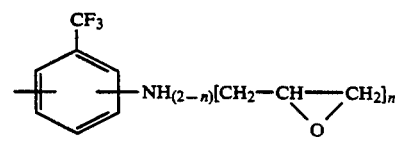

where n is 1 or 2, m is 0, 1, or 2, X is Y or

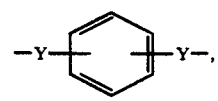

and Y is —, O, S, SO, SO$_2$, CO, C(CH$_3$)$_2$, or C(CF$_3$)$_2$. An epoxy resin can be made by mixing the glycidyl diamine with an epoxy curing agent. The epoxy resins can be used as adhesives or to make composites.

20 Claims, No Drawings

GLYCIDYL DIAMINES CONTAINING AROMATIC TRIFLUOROMETHYL GROUP AND EPOXY RESINS PREPARED THEREFROM

BACKGROUND OF THE INVENTION

This invention relates to glycidyl diamines, epoxy resins containing the glycidyl diamines, cured epoxy resins, and composites formed from the epoxy resins. In particular, it relates to compounds having two aromatic rings and a trifluoromethyl group and up to two amino glycidyl groups on each aromatic ring.

Epoxy resins are widely used as adhesives and in making composite materials. Epoxies based on aromatic amines have been made in order to obtain enhanced properties. See, for example, U.S. Pat. No. 4,451,645. The composite matrix most widely used in high performance fiber prepreg composites is composed of N,N,N',N'-tetraglycidyl(4,4'-methanobis[benzenamine]) and a 4,4'-diaminodiphenyl sulfone (DDS) hardener.

One of the major problems with this material, and with epoxy resins in general, is the formation of microcracks and the subsequent loss of mechanical properties in the harsh environments encountered in aerospace industrial applications. This micromechanical damage is believed to be due to the absorption of water, which is reported to act as plasticizer for epoxies. Due to plastization by the molar dilution by water, epoxy glass transition temperatures ($T_g$) typically drop 10° to 20° C. for every 1 wt% water absorbed.

SUMMARY OF THE INVENTION

We have discovered that epoxy resins prepared from glycidyl diamines having one to four aromatic amino diglycyl groups and at least two aromatic trifluoromethyl groups have a number of unexpectedly superior properties, particularly ease of processing and a significantly low moisture absorption. In addition, the epoxy resins of this invention have high glass transition temperatures, low dielectric constants, good thermal stabilities, low flammabilities, and high toughness.

DESCRIPTION OF THE INVENTION

The glycidyl diamines of this invention have the formula

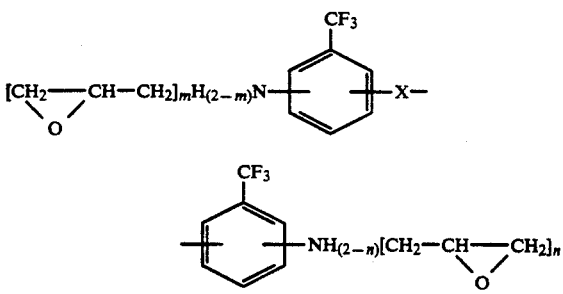

where n is 1 or 2, m is 0, 1, or 2, X is Y or

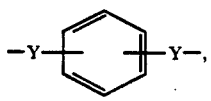

and Y is —, O, S, SO, $SO_2$, CO, $C(CH_3)_2$, or $C(CF_3)_2$. In the preferred glycidyl diamines X is — or O and n is 1 or 2 and m is 2 because their diamine precursors can be synthesized in practical quantities.

The glycidyl diamines can be made, for example, by reacting a solution of the corresponding non-glycidyl diamine with epichlorohydrin in the presence of alkali. From one to four equivalents of epichlorohydrin can be used, depending on the number of glycidyl groups one wants on the diamine. The product is a mixture of glycidyl diamines having 1 to 4 glycidyl groups, but the average number of glycidyl groups depends upon the number of equivalents of epichlorohydrin used. The reaction of the diamine with the epichlorohydrin produces hydrochloric acid, which reacts with the alkali. The amount of alkali used should be slightly in excess (up to about 15wt% excess) of the amount stoichiometrically required to react with the hydrochloric acid formed. The reaction proceeds at a temperature from about room temperature to about the boiling point of the solvent and is complete after about 2 to about 48 hours. The glycidyl diamine produced can be removed from the aqueous reaction mixture by the addition of a water-immiscible solvent for it, such as toluene.

Some of the diamines from which the glycidyl diamines are prepared can be purchased, while others must be made. For example, 3,5-diaminobenzotrifluoride can be prepared by the catalytic hydrogenation of 3,5-dinitrobenzotrifluoride and the preparation of 4,4'-oxybis[3-(trifluoromethyl)benzenamine]is given in R.A. Buchanan et al., Polymer Preprints, 32(2), 193 (1991), herein incorporated by reference. Examples 1, 2, and 3, which follow, illustrate the preparation of three other diamines.

The glycidyl diamines can be stored indefinitely. When it is desired to use a glycidyl diamine to prepare an epoxy resin, it is mixed with a hardener (epoxy curing agent). Any epoxy hardener can be used with glycidyl diamines of this invention. Typical epoxy hardeners include anhydrides, dianhydrides, amines, diamines, mercaptans, and phenols. Diamine hardeners are preferred, and the preferred diamine hardener is

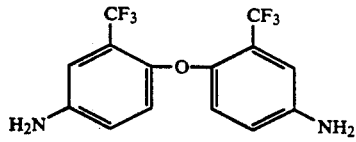

because it adds additional trifluoromethyl groups to the cured resin. From 50 to about 100% of a hardener is typically used.

The composition of the glycidyl diamine and hardener (the "epoxy resin") can be used as an adhesive by spreading it between substrates and curing it. The epoxy resin can bond together metals such as aluminum, which are difficult to bond by other means. The epoxy resin can also be used as a composite by mixing it with a filler such as glass fibers or graphite fibers, pressing the mixture into a shape, and then curing. About 10 to about 60 wt% of a filler is typically used with the epoxy resin. Other uses for the epoxy resins of this invention include laminations, castings, and moldings. The epoxy resin can be cured at temperatures from about 150° C. to about 250° C.

The following examples further illustrate this invention.

EXAMPLE 1

5,5'-Oxybis[3-(trifluoromethyl)benzenamine]

3,5-Dinitrobenzotrifluoride (25.1 g) and potassium fluoride (21.2 g) were refluxed in dimethyl formamide for 24 hours. The reaction mixture was poured into water. The aqueous solution was extracted with ether and cooled to 5° C. to obtain 11.3 grams of 3,3'-bis[trifluoromethyl]-5,5'-dinitro diphenyl ether. The material was purified by recrystallization from toluene and ethanol; mp=127°-128° C. The nitro groups were reduced using hydrazine hydrate and 10% palladium on carbon in ethanol at 45° C. The diamine was obtained as an oil which crystallized upon standing; mp=62°-63° C.

EXAMPLE 2

5,5'-Sulfonylbis3-(trifluoromethyl) benzenamine]

Thiobis[3-(trifluoromethyl)benzene](Aldrich Chemical, 10 g) was nitrated with fuming nitric acid (78 g) and 20% oleum (90 mL) at 10° C. for 1.5 hours, then at 65° C. for 3 hours. The reaction mixture was poured onto ice and the resulting solid collected. The solid was washed with water and recrystallized from toluene to obtain 7.16 g (52%) of 3,3'-bis[trifluoromethyl]-5,5'-dinitro diphenyl sulfone; mp=204° C. The nitro groups were reduced using hydrazine hydrate and 10% palladium on carbon in ethanol. The diamine was obtained as an off-white solid; mp=181°-183° C.

EXAMPLE 3

5,5'-Carbonylbis[3-(trifluoromethyl) benzenamine]

Carbonylbis[3-(trifluoromethyl)benzene] (Aldrich Chemical, 41 g) was nitrated with fuming nitric acid (34 g) and 20% oleum (83 mL) at 40° C. for 3 hours. The reaction mixture was poured onto ice and the resulting solid collected. The solid was washed with water and recrystallized from toluene to obtain 51 g (82%) of 3,3'-bis[trifluoromethyl]-5,5'-dinitrobenzophenone; mp=181° C. The nitro groups were reduced using iron powder and HCl in ethanol. The diamine was obtained as a beige powder.

EXAMPLE 4 (COMPARISON EXAMPLE)

Preparation of N,N,N',N'-Tetraglycidyl(3,5-diaminobenzotrifluoride) (35-DABTF resin)

A mixture of 3,5-diaminobenzotrifluoride (116.9 grams, 0.66 moles), epichlorohydrin (491.5 grams, 5.31 moles), water (35 grams) and 95 wt% ethanol (257 grams) was heated in a resin kettle at 80° C. After 6 hours, the temperature was lowered to 60° C. and 30wt% sodium hydroxide solution (445 grams, 3.34 moles) was added over a 1 hour period. The mixture was heated an additional 3.5 hours at 60° C. The volatile components were removed by evaporative distillation at 60° C. and 30 mm. The resin was dissolved in toluene (585 mL) and washed four times with water (750 mL, 500 mL, 500 mL and 500 mL). Removal of the toluene and the residual water by evaporative distillation provided an amber resin (262.3 grams, 98.8 wt%). The weight of the resin per epoxide was 125.6 using the method described by W. Liu, E.M. Pearce and T.K. Kwei; J. Appl. Pol. Sci. 30 2907 (1985). The epoxy content of the 35-DABTF resin sample was 80%.

EXAMPLE 5

Preparation of N,N,N',N'-Tetraglycidyl(4,4'-oxybis3-(trifluoromethyl)benzenamine]) (124-OBABTF resin)

A mixture of 4,4-oxybis[3-(trifluoromethyl) benzenamine]) (124-OBABTF, 220 grams, 0.65 moles), epichlorohydrin (606 grams, 6.55 moles), water (66 grams) and 95 wt% ethanol (484 grams) was heated in a resin kettle at 60° C. After 6 hours, 30 wt% sodium hydroxide solution (436 grams, 3.27 moles) was added over 1 hour. The mixture was heated an additional 6 hours at 60° C. The volatile components were removed by evaporative distillation at 60° C. and 40 mm. The resin was dissolved in toluene (585 mL) and washed three times with water (750 mL, 500 mL and 500 mL). Removal of the toluene and the residual water by evaporative distillation provided an amber resin (366.2 grams, 100 wt%). The weight of the resin per epoxide was 172 using the method described by W. Liu, E.M. Pearce and T.K. Kwei; J. Appl. Pol. Sci. 30 2907 (1985). The epoxy content of the 124-OBABTF resin sample was 82%.

EXAMPLE 6 (COMPARISON EXAMPLE)

Cured 35-DABTF Resin

35-DABTF resin (from Example 1, 5.7 grams), phthalic anhydride (3.0 grams) and tris(dimethylaminomethyl) phenol (0.04 gram) were combined and the mixture was heated at 160° C. for 1.5 hours to produce a hardened epoxy resin.

EXAMPLE 7

Cured 124-OBABTF Resin

124-OBABTF resin (from Example 2, 4.8 grams), phthalic anhydride (3.6 grams) and tris(dimethylaminomethyl)phenol (0.05 gram) were combined and the mixture was heated at 160° C. for 2 hours to produce a hardened epoxy resin.

EXAMPLE 8 (COMPARISON EXAMPLE)

Preparation of N,N,N',N'-Tetraglycidyl(4,4'-oxybis[benzenamine]) (4,4'-ODA resin)

Example 2 was repeated using 4,4-oxybis[benzenamine]instead of 4,4-oxybis[3-(trifluoromethyl)benzenamine]. Yield=100%.

EXAMPLE 9 COMPARISON EXAMPLE)

Several attempts were made to prepare N,N,N',N'-tetraglycidyl(4,4'-methanobis[3-trifluoromethyl]benzenamine) using the procedure of Example 4 of U.S. Pat. No. 4,451,645, but a good product could not be made. The procedure of the patent was followed, except that the product was not purified by high pressure liquid chromatography (HPLC) due to poor solubility properties. The product was a brittle white solid. The method of U.S. Pat. No. 4,451,645 cannot be used to prepare tetraglycidyl diamines where the link between the aromatic rings is not methylene.

EXAMPLE 10

Cured Resins

3mm thick epoxy resin castings were made from the resins described above using 4,4'-diaminodiphenyl sulfone (DDS) (0.62 equivalents) as the curing agent. The DDS and resin mixture was heated in molds at 150° C.

for one hour and 170° C. for five hours. The hardened resin was removed from the mold and post-cured at 200° C. for 4 hours.

The following table gives the results of tests performed on these castings:

| Resin | Tensile Strength (kpsi) | Tensile Modulus (kpsi) | Glass Transition Temp. (°C.) | Heat Deflection Temp. (°C.) |
|---|---|---|---|---|
| "MY-720"* | 9.53 | 4,540 | 261 | 245 |
| 124-OBABTF-Resin | 6.51 | 4,700 | 231 | 228 |
| 4,4'-ODA Resin | 9.36 | 5,320 | 235 | 208 |
| 35-DABTF-Resin | 6.43 | 4,850 | 243 | 212 |

*N,N,N',N'-tetraglycidyl (4,4'-methanobis [benzenamine]) from Ciba-Geigy

In the above table, the tensile properties were determined using ASTM test D638 and the heat deflection temperature was determined using ASTM test D648.

Additional resins were similarly prepared using 4,4'-oxybis[3-(trifluoromethyl)benzenamine] (124-OBABTF), m-phenylene diamine (MPDA), or 3,5-diaminobenzotrifluoride (35-DABTF) as curing agents. The moisture absorption of these resins was compared to that of resins prepared using a DOS hardener. Using ASTM test D570, samples of the cured resins were weighed, boiled in water for one week, and re-weighed to determined moisture absorption. The following table gives the results.

| Glycidyl Diamine | Hardener | % Weight Gain |
|---|---|---|
| 124-OBABTF | DDS | 3.4 |
| 124-OBABTF | 124-OBABTF | 2.7 |
| 124-OBABTF | 35-DABTF | 3.2 |
| 124-OBABTF | MPDA | 3.7 |
| 4,4'-ODA | DDS | 7.7 |
| "MY-720" | DDS | 4.7 |
| "MY-720" | 124-OBABTF | 3.5 |
| "MY-720" | 35-DABTF | 4.0 |
| "MY-720" | MPDA | 4.1 |
| 35-DABTF | DDS | 6.1 |
| 35-DABTF | 124-OBABTF | 4.8 |
| 35-DABTF | 35-DABTF | 5.8 |
| 35-DABTF | MPDA | 7.6 |

The above table shows that the order of moisture absorbed was, in general:

124-OBABTF-Resin < "MY-720"
< 35-DABTF-Resin < 4,4'-ODA-Resin

We claim:

1. A glycidyl diamine having the formula

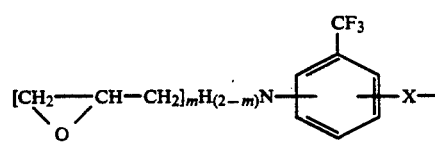

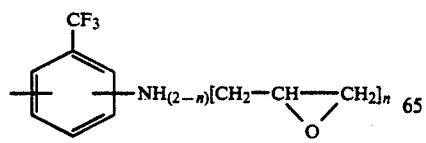

where n is 1 or 2, m is 0, 1, or 2, X is Y or

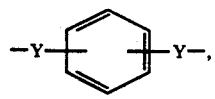

and Y is —, O, S, SO, $SO_2$, CO, $C(CH_3)_2$ or $C(CF_3)_2$.

2. A glycidyl diamine according to claim 1 wherein n is 1 and m is 1.

3. A glycidyl diamine according to claim 1 which has the formula

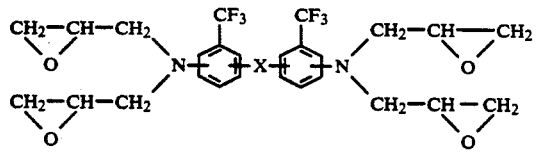

4. A glycidyl diamine according to claim 1 wherein X is —.

5. A glycidyl diamine according to claim 1 wherein X is O.

6. A glycidyl diamine according to claim 1 which has the formula

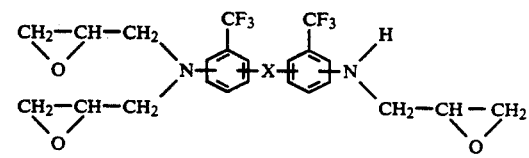

7. A glycidyl diamine according to claim 6 wherein X is —.

8. A glycidyl diamine according to claim 6 wherein X is O.

9. A composition comprising an epoxy curing agent and a glycidyl diamine having the formula

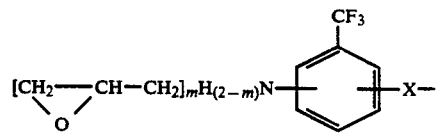

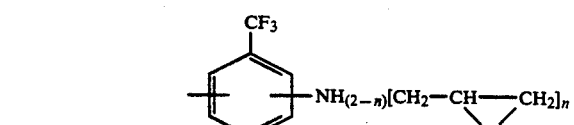

where n is 1 or 2, m is 0, 1, or 2, X is Y or

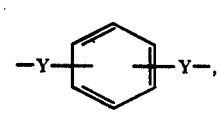

and Y is —, O, S, SO, $SO_2$, CO, $C(CH_3)_2$, or $C(CF_3)_2$.

10. A composition according to claim 9 wherein said glycidyl diamine has the formula

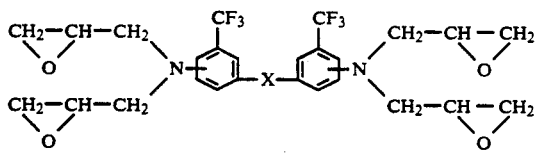

11. A composition according to claim 10 wherein x is —.

12. A composition according to claim 10 wherein x is O.

13. A composition according to claim 9 wherein said glycidyl diamine has the formula

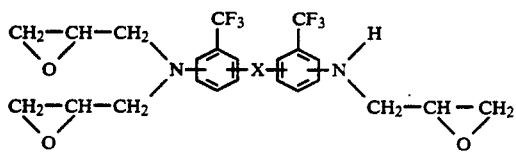

14. A composition according to claim 13 wherein x is —.

15. A composition according to claim 13 wherein x is O.

16. A composition according to claim 9 wherein said epoxy curing agent has the formula

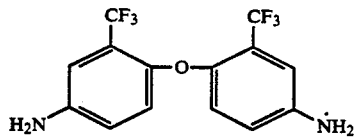

17. A composition according to claim 9 including about 10 to about 60 wt% of a glass filler.

18. A composition according to claim 9 in a cured state.

19. A glycidyl diamine according to claim 1 which has the formula

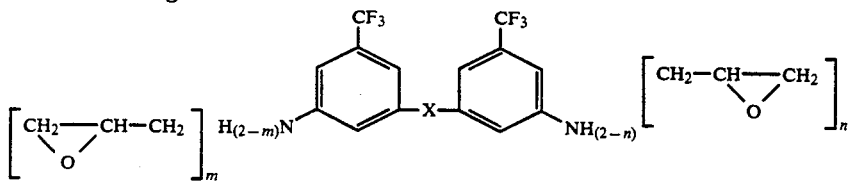

20. A composition according to claim 9 wherein said glycidyl diamine has the formula

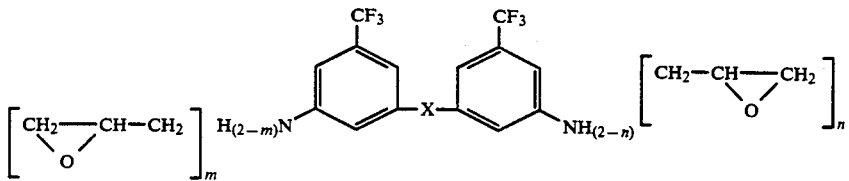

* * * * *